United States Patent
Chung et al.

(10) Patent No.: US 6,316,644 B1
(45) Date of Patent: Nov. 13, 2001

(54) PILYETHOXYLATED RETINAMIDE DERIVATIVES AND PROCESS FOR PREPARING THE SAME

(75) Inventors: Bong Youl Chung; Young Keun Kim; In Sang Lee; Bong Jun Park; Wan Goo Cho; Young Sook Song; Mun Eok Park; Young Deuk Kim; Sung Jun Lee, all of Taejeon (KR)

(73) Assignee: LG Chemical Ltd., Seoul (KR)

( * ) Notice: Subject to any disclaimer, the term of this patent is extended or adjusted under 35 U.S.C. 154(b) by 0 days.

(21) Appl. No.: 09/647,483

(22) PCT Filed: Feb. 4, 1999

(86) PCT No.: PCT/KR99/00056

§ 371 Date: Sep. 27, 2000

§ 102(e) Date: Sep. 27, 2000

(87) PCT Pub. No.: WO99/50240

PCT Pub. Date: Oct. 7, 1999

(30) Foreign Application Priority Data

Mar. 30, 1998 (KR) .................................. 98-11079

(51) Int. Cl.$^7$ .......................... C07C 233/00; C07C 231/00

(52) U.S. Cl. .................................. 554/64; 554/68; 554/69; 514/625; 514/627

(58) Field of Search .................................. 544/64, 68, 69; 514/625, 627

*Primary Examiner*—Deborah D. Carr
(74) *Attorney, Agent, or Firm*—Peter F. Corles; Christine C. O'Day; Edwards & Angell, LLP

(57) ABSTRACT

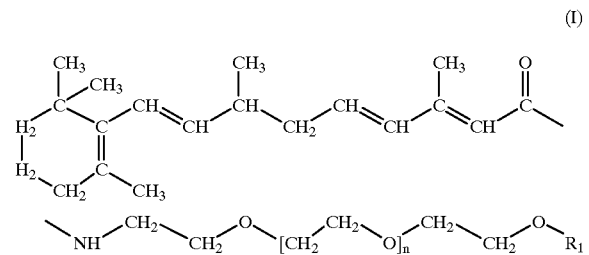

The present invention relates to a polyethoxylated retinamide derivative represented by formula (I), which is useful as an agent for inhibiting skin aging; in R represents hydrogen or $C_{1-6}$ lower alkyl and n denotes the number of 2 to 100, and the process for preparing the compound of formula (I) as an effective component.

9 Claims, 2 Drawing Sheets

RA ; Retinoic Acid, Vit. –REG ; Compound of Formula (1), Vit. –PAL ; Retinol Palmitate RA ; Retinoic Acid, Vit.-REG ; Compound of Formula (1), Vit.-PAL ; Retinol Palmitate

PILYETHOXYLATED RETINAMIDE DERIVATIVES AND PROCESS FOR PREPARING THE SAME

This application is a 371 of PCT/KR99/00056 filed Feb. 4, 1999.

TECHNICAL FIELD

The present invention relates to a polyethoxylated retinamide derivative represented by the following formula (I), which is useful as an agent for inhibiting skin aging:

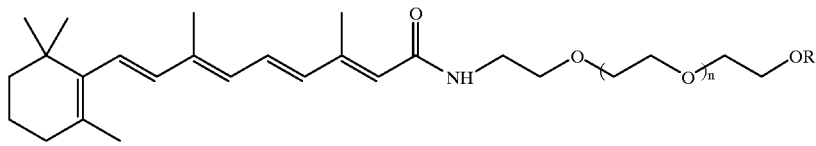

(I)

in which

R represents hydrogen or $C_{1-6}$-lower alkyl and n denotes the number of 2 to 100, and a process for preparing the compound of formula (I).

The 13-trans-polyethoxylated retinamide derivatives of formula (I) according to the present invention are non-irritable and exhibit an enhanced skin absorption and collagen synthesis property. Therefore, the compounds of formula (I) can be effectively used as the functional raw material in the pharmaceutical and cosmetic products. Thus, the present invention also relates to a cosmetic composition which comprises the compound of formula (I) as an effective component.

BACKGROUND ART

The exposure of skin to sun light for a long period may cause the characteristic signs of skin photoaging, for example, wrinkles, skin roughness, freckles, etc. and further numerous skin imbalance conditions including skin cancer such as keratosis.

It has been reported that such skin photoaging can be improved by applying the cream preparation containing tretinoin (all-trans-retinoic acid) to skin [see, "Topical Tretinoin Improves Photoaged Skin", *JAMA*, 259, Vol. 4, pp95, 527–532, Jan, 22/29, 1988, the authors Webb et. al.]. However, since tretinoin is lipid-soluble, it has a low skin absorption and is unstable in the living body and irritable to skin, and further may cause the side effects such as skin xerosis, wound, peeling-off, etc. Due to such side effects tretinoin can be used as the main raw material for pharmaceutical and cosmetic products only with many difficulties. Therefore, it has been urgently required to develop the new functional raw material which still posseses the activity of tretinoin for inhibiting the photoaging and is non-irritable.

As one of the more improved agents for inhibiting skin aging over tretinoin, it has been reported that ester or amide derivatives of 13-/trans-retinoic acid exhibit a therapeutic effect for treating skin disorders and acne. Specifically, it has been reported that 2-(all-trans-retinoyloxy)-4-methoxyacetophenone compound has a relatively low irritability and exhibits an effect of inhibiting skin cancer and photoaging [see, U.S. Pat. No. 4,677,120]; and the compound obtained from esterification of retinoic acid and tetraethylene glycol shows an increase in skin penetrating effect [see, U.S. Pat. No. 4,900,478]. In addition, it has also been reported that N-(4-hydroxy-phenyl)retinamide (4-HPR) and retinoyl β-glucuronide (RAG) maintain the activity of retinoic acid but have a relatively reduced toxicity [see, *FASEB J.*, 10, 1014–1024, 1996].

However, since the above-mentioned esters and amides of retinoic acid are lipid soluble and therefore, naturally have a weak skin absorptivity, it is difficult to much expect an increase in collagen synthesis and an effect of inhibiting elastin decomposition. Further, it has also been indicated that they have the stability problem due to their rapid enzymatic decomposition in the living body. Therefore, although these ester and amide derivatives of retinoic acid may overcome the irritability, which is the typical disadvantage involved in use of the prior retinoid-based raw materials for inhibiting skin aging, to some extent, a desire for the new agent for inhibiting skin aging, which has an increased absorptivity through skin, a maximized cell regeneration ability and an improved stability, still remains.

Thus, the present inventors have extensively studied to resolve the problems involved in the prior retinoid-based skin aging inhibitors and noticed that polyethylene glycol deriatives not only have an excellent surface activating property and an effect of increasing the skin absorptivity due to their hydrophilicity but also have the desirable property of minimizing the residual toxicity because they are dissolved in water so that they can be readily excreted out of the body. According to this, we have developed the novel polyethoxylated retinamide derivative of formula (I) which is obtained by amide condensation of a polyethylene glycol derivative and a retinoic acid derivative. The compound of formula (I) thus developed has a superior chemical stability and skin absorptivity over the prior retinoic acid derivatives and consequently, exhibits an excellent skin regeneration effect.

DISCLOSURE OF THE INVENTION

Therefore, the purpose of the present invention is to provide a polyethoxylated retinamide derivative represented by the following formula (I), which can be effectively used as an agent for inhibiting skin aging:

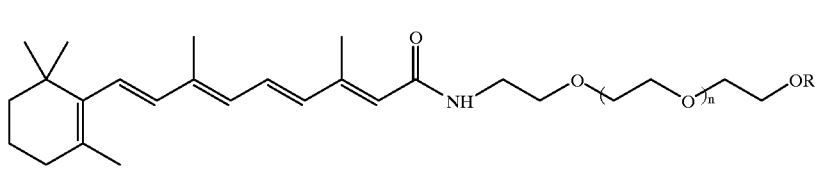

(I)

in which

R represents hydrogen or $C_{1-6}$-lower alkyl and n denotes the number of 2 to 100.

Another purpose of the present invention is to provide a process for preparing the compound of formula (I) as defined above.

Still another purpose of the present invention is to provide a cosmetic composition which comprises the compound of formula (I) as an effective component.

BRIEF DESCRIPTION OF DRAWINGS

For a thorough understanding of the nature and objects of the invention, reference should be made to the following detailed description taken in connection with the accompanying drawings in which.

DETAILED DESCRIPTION OF THE INVENTION

Figure 1:
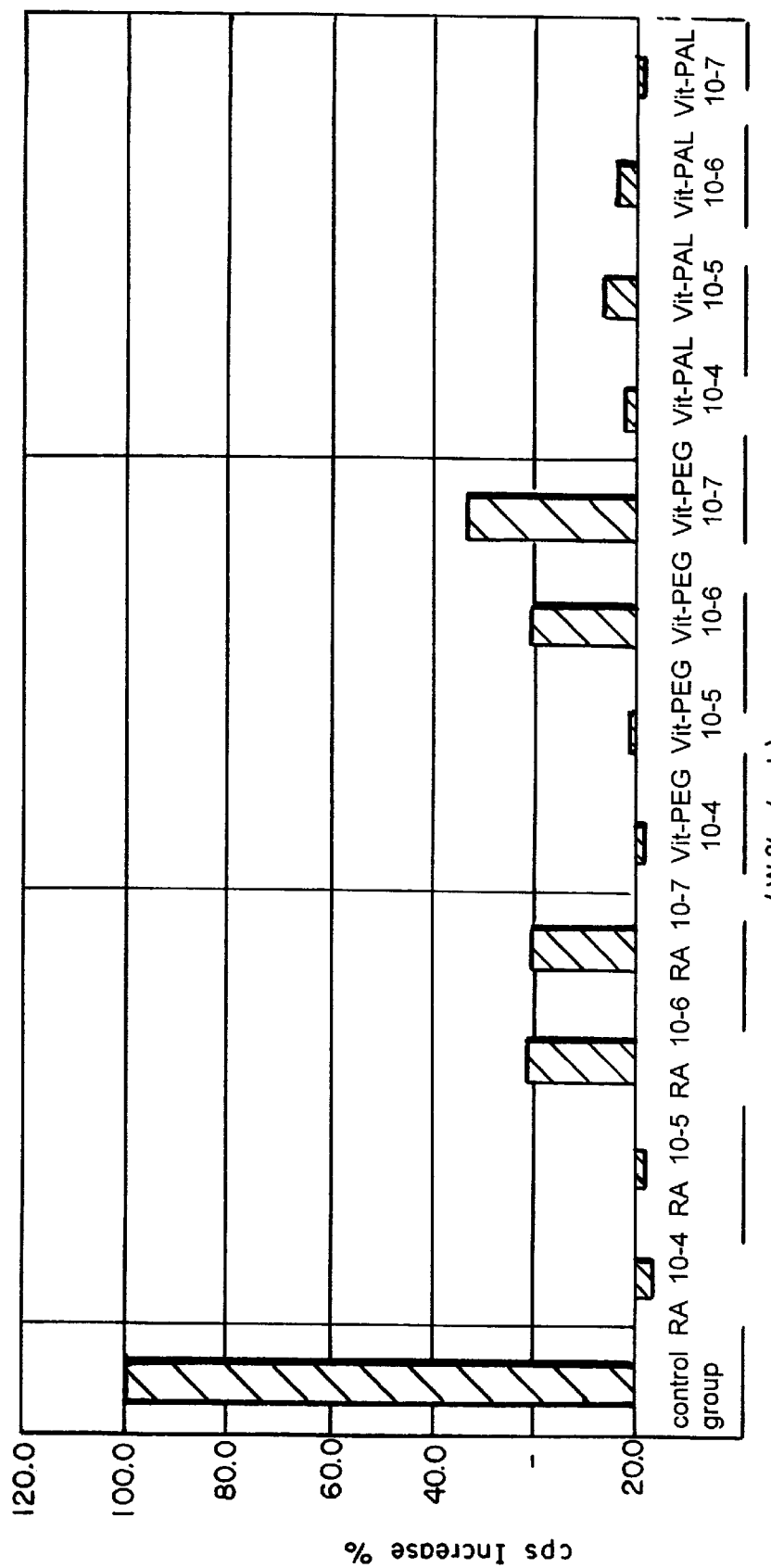
FIG. 1 shows the rate of increase in collagen synthesis by the compound of formula (I) according to the present invention in comparison to those of retinoic acid and retinol palmitate as the comparative materials.

The present invention relates to a polyethoxylated retinamide derivative represented by the following formula (I):

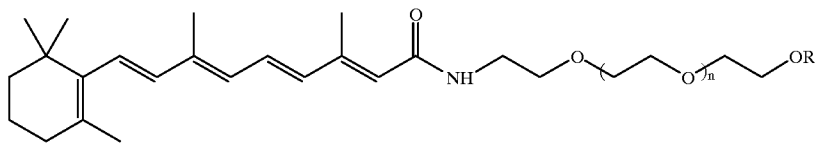

(I)

in which

R represents hydrogen or $C_{1-6}$-lower alkyl and n denotes the number of 2 to 100.

Among the compound of formula (I) as defined above, the compounds wherein R is hydrogen or methyl and n is the number of 4 to 40 are more preferable.

In addition, the present invention provides a process for preparing the novel compound of formula (I). The compound of formula (I) can be prepared by the process which comprises:

1) reacting a compound of formula (IIa):

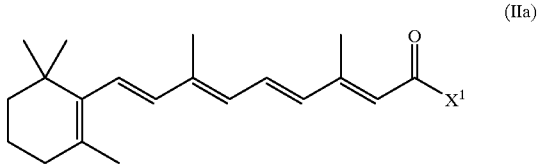

(IIa)

wherein $X^1$ represents halogen, with a mono-methoxy polyethylene glycol amine of formula (IIIa):

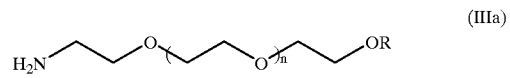

(IIIa)

wherein R and n are defined as above, in a solvent in the presence of an organic amine catalyst, or 2) reacting a compound of formula (IIb):

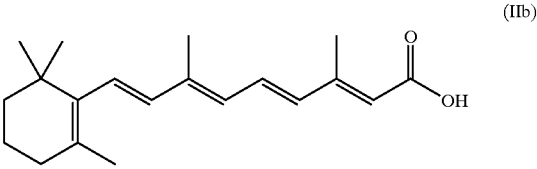

(IIb)

with a compound of formula (IIIa):

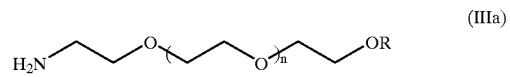

(IIIa)

wherein R and n are defined as above, in a solvent in the presence of a condensing agent and a catalyst, or 3) reacting a compound of formula (IIc):

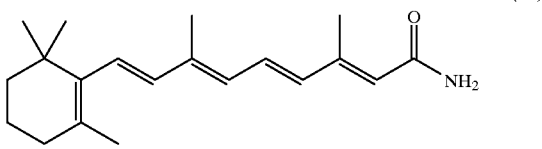

with a mono-methoxy polyethylene glycol halide or sulfonate of formula (IIIb):

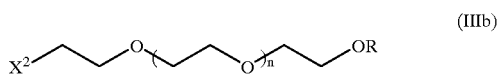

wherein R and n are defined as above and $X^2$ is halogen, p-toluenesulfonyl or methanesulfonyl, in a solvent in the presence of a base.

The above processes are more specifically explained hereinafter.

In the variant 1), pyridine or triethylamine is preferably used as the organic amine which acts as the catalyst, and an anhydrous organic solvent, for example, one or more selected from the group consisting of dichloromethane, benzene, toluene, tetrahydrofuran and diethyl ether can be preferably used as the solvent. In this process, the organic amine is preferably used in the ratio of 1.0 to 2.0 moles with respect to one mole of the compound of formula (IIIa).

In the variant 2), N,N-carbonyldiimidazole (CDI) or N,N-dicyclohexylcarbodiimide (DCC) is used as the condensing agent, and N,N-dimethylaminopyridine (DMAP) or 1-hydroxybenzotriazole (HOBT) is preferably used as the catalyst for condensation reaction. In addition, the same solvent as previously mentioned in relation to the variant 1) can also be preferably used as the solvent in this process. The reaction is generally conducted in nitrogen atmosphere under shading and anhydrous condition. The reaction is carried out under cooling and warming condition.

As the base in the variant 3), one or more selected from the group consisting of metal bases such as sodium hydride, sodium hydroxide, potassium hydride, sodium carbonate and potassium carbonate and organic bases such as pyridine and triethylamine can be preferably used. In this process, the same solvent as previously mentioned in relation to the variant 1) can also be used as the solvent.

However, it should be understood that the base, condensing agent, catalyst and solvent which can be used in the processes according to the present invention are not limited to those as mentioned above and any of the known reagents conventionally used for the same purpose in the relevant technical field can be used in the present invention unless they adversely affect the reaction.

The halide compound of formula (IIa) which is used as the starting material in the process according to the present invention can be prepared by reacting a carboxylic acid compound of formula (IIb) with a halogenating agent such as phosphorus trichloride, thionyl chloride, etc.; and the polyethylene glycol derivative of formula (IIIa) or (IIIb) can be readily prepared according to the known methods [see, ① S. Zalipsky, C. Gilon and A. Zilkha, *Eur. Polym. J.*, Vol. 19, No. 12, pp1177–1183. 1983, and ② J. Milton. Harris, N. H. Hundley, T. G. Shannon and E. C. Struck, *J. Org. Chem.*, 1982, 47, 4789–4791] [Please refer to Example 1(B)].

The compound of formula (I) prepared according to the above process can be purified by any of conventional separation and purification techniques, for example, recrystallization or column chromatography.

The compound of formula (I) can be used for treatment of wrinkles and freckles caused by skin disorders such as skin cancer and acne. Particularly, the compound of formula (I) has characteristic features that it does not cause skin irritation upon application to skin, and due to its high skin absorptivity, exhibits a maximized collagen synthesis and a skin regeneration effect through inhibition of elastin decomposition.

The tests for identification of pharmacological activities of the compound of formula (I) according to the present invention were conducted as follows. First, the test for percutaneous absorption was carried out by cutting off the dorsal skin from 8-weeks aged female mouse, applying the test sample (35 mM) to the skin and then analysing the percutaneous absorption of the test sample by means of an apparatus for measuring percutaneous absorption (Franz cell) and HPLC. The cytotoxicity test was carried out by MTT assay method using V79-4 cells. The test for skin irritability was carried out at the concentration of the test sample in the range of 0.1 to 1% by using the O/W formulation of water and propylene glycol and Lexol GT-865 through the patch test in guinea pigs. The test for organ incubation of skin was carried out by MTT assay method using naked female mouse. The allergy test was conducted in Balb/c mouse by using ethanol as the carrier vehicle. In addition, the cell regeneration effect was determined by measuring the effect of increasing collagen synthesis in human fibroblasts.

According to the result of the above-mentioned tests, it has been identified that in comparison to retinoic acid and retinol palmitate which have been previously and commercially used as the pharmaceutical and cosmetic raw materials for inhibiting skin aging, the compound of formula (I) according to the present invention exhibits an 2–10 times increase in percutaneous absorption and is non-toxic at the concentration of $10^{-4}$ w %/ml and below in the cytotoxicity test. Therefore, since the compound of formula (I) has, as well as non-toxic and non-irritable properties, a maximized skin absorption property and therefore, a superior activity for increasing collagen synthesis, it can be conveniently used as an additive for inhibiting skin aging in pharmaceutical and cosmetic products (formulations such as creams, lotions, gels, etc.).

The present invention is more specifically illustrated on the basis of the following examples and experiments. However, it should be understood that these examples and experiments are provided for more clear understanding of the present invention and are not intended to limit the scope of the present invention thereto in any sense.

EXAMPLE 1

Preparation of polyethoxylated retinamide of formula (I) (R=methyl, n=9.8)

(A) 3.41 g (0.0165 mole) of dicyclohexylcarbodiimide (DCC) was added to 50 ml of dry dichloromethane solution of 6.98 g (0.0126 mole) of 1-amino-polyethyleneglycol-monomethyl ether (formula (IIIa), mean molecular weight 550), 4.54 g (0.0151 mole) of retinoic acid and 1.7 g (0.0126 mole) of 1-hydroxybenzotriazole and then stilled at room temperature for 8 hours in nitrogen atmosphere under shading and anhydrous condition. The reaction solution was filtered and then the solvent was removed by distillation under reduced pressure. The residue was separated by column chromatography ($SiO_2$, mesh size 270–400, dichloromethane/methanol=15:1, v/v) to obtain 9.42 g (Yield 75%) of the title compound (pale yellow liquid in the form of wax, Tm=−15° C., Rf=0.22).

(B) 1-Amino-polyethyleneglycol-monomethyl ether (formula (IIIa)) used as the starting material in the above (A) was prepared from polyethylene glycol monomethyl ether via three-steps procedure as follows.

i) 55 g (0.1 mole) of polyethylene glycol monomethyl ether was dissolved in 300 ml of toluene and then distilled and dried. To the residue was added 7.9 g (0.1 mole) of dry pyridine. The reaction solution was heated under reflux while 7.3 ml of thionyl chloride was added dropwise over 30 minutes. After the addition is completed, the reaction solution was heated under reflux for 4 hours and then cooled to room temperature. The reaction solution was filtered to remove pyridine hydrochloride and then toluene was removed under reduced pressure. The residue was dissolved in dichloromethane, dried over anhydrous potassium carbonate and then filtered. The filtrate was treated with activated alumina (100 g), filtered and then distilled under reduced pressure to obtain 56 g (Yield 99%) of chloro-polyethylene glycol monomethyl ether [$MPEG_{550}$-Cl] (Tm=−10° C., colorless liquid).

ii) 56 g (0.099 mole) of $MPEG_{550}$–Cl obtained in the step was dissolved in 300 ml of dimethylformamide (DMF). To the resulting solution was added 51.2 g (0.79 mole) of sodium azide ($NaN_3$) and then heated at 120° C. for 3 hours. The reaction solution was cooled, filtered and then distilled under reduced pressure to remove DMF. The residue was dissolved in dichloromethane and washed with water. The organic layer was separated, dried over anhydrous magnesium sulfate, filtered and then distilled under reduced pressure to obtain 55 g (Yield 98%) of azido-polyethylene glycol monomethyl ether [$MPEG_{550}$–$N_3$] (Tm=−11° C., colorless liquid).

iii) 55 g of $MPEG_{550}$–$N_3$ obtained in the step ii) and 28.4 g (0.107 mole) of triphenyl phosphine ($Ph_3P$) were dissolved in 300 ml of tetrahydrofuran and 3 ml of water was then added thereto. The reaction mixture was stirred at room temperature for 8 hours. The reaction solution was distilled under reduced pressure to remove the solvent, and the residue was dissolved in dichloromethane and then washed with water. The organic layer was separated, dried over anhydrous magnesium sulfate, filtered and then distilled under reduced pressure. The resulting mixture was passed through silica gel [$SiO_2$](300 g) to remove the side product, triphenylphosphine oxide, and then distilled under reduced pressure to obtain 45 g (Yield 85%) of 1-amino-polyethylene glycol monomethyl ether [$MPEG_{550}$–$NH_2$] (pale yellow liquid, Tm=−12° C.) (see, *Bioconjugate Chem.*, Vol. 7, No. 2, 1996).

EXAMPLE 2

Preparation of polyethoxylated retinamide of formula (I) (R=methyl, n=9.8)

4.0 g (0.013 mole) of retinoic acid was dissolved in 20 ml of dry toluene and then 1.83 g (0.013 mole) of phosphorus trichloride ($PCI_3$) was added dropwise thereto. The reaction mixture was stirred at room temperature for 15 hours in nitrogen atmosphere under shading and anhydrous condition.

The solution of retinoic acid chloride as obtained above was added together with 7.15 g (0.013 mole) of 1-amino-polyethylene glycol monomethyl ether obtained in Example 1(B) and 1.57 g (0.016 mole) of triethylamine dropwise to 40 ml of dry methylene chloride over 20 minutes under ice cooling, and the mixture was then continuously stirred at room temperature for 5 hours. The reaction solution was added to 50 ml of saturated sodium chloride. The organic layer was separated, washed with water, dried over sodium sulfate, filtered and then concentrated. The residue was separated by column chromatography (silica, mesh size 200–400, methylene chloride/methanol=15:1, v/v) to obtain 9.1 g (Yield 86%) of the title compound as a pale yellow product.

EXAMPLE 3

Preparation of polyethoxylated retinamide of formula (I) (R=methyl, n=9.8)

(A) The solution of 3 g (0.01 mole) of retinamide in 20 ml of dry toluene was added dropwise to the solution of 0.58 g (0.012 mole) of sodium hydride in 10 ml of dry toluene under ice cooling and then stirred at room temperature for 4 hours. To the reaction mixture was added dropwise the solution of 7.11 g (0.01 mole) of monomethoxy polyethylene glycol p-toluene- sulfonate in 20 ml of dry toluene over 10 minutes and then stirred at room temperature for 10 hours. The reaction solution was distilled under reduced pressure and then concentrated. The residue was separated by column chromatography (silica, mesh size 200–400, methylene chloride/methanol=15:1, v/v) to obtain 6.9 g (Yield 82%) of the title compound as a pale yellow product.

(B) The retinamide (formula (IIc)) used as the starting material in the step (A) above was prepared from retinoic acid as follows.

10 g (0.031 mole) of retinoic acid chloride as prepared according to the procedure described in Example 2 was added to the mixture of 300 ml of ammonia water (35%) and 100 ml of tetrahydrofuran and then stirred at room temperature for 20 hours. The reaction solution was distilled under reduced pressure and then concentrated. The residue was extracted with methylene chloride. The organic layer was separated, washed with water, dried over anhydrous magnesium sulfate, filtered and then distilled under reduced pressure to obtain 9.43 g (Yield 99%) of the desired retinamide.

EXAMPLE 4

Preparation of polyethoxylated retinamide of formula (I) (R=hydrogen, n=9.8)

3 g (0.0146 mole) of dicyclohexylcarbodiimide (DCC) was added to the solution of 4.48 g (0.0112 mole) of 1-amino-polyethylene glyco (molecular weight 400), 3.98 g (0.0133 mole) of retinoic acid and 1.51 g (0.0112 mole) of 1 -hydroxybenzotriazole in 40 ml of dry dichloromethane, and the reaction solution was then treated according to the same procedure as described in Example 1(A) to obtain the title compound (Yield 62%, Tm=−14° C., Rf=0.15).

EXAMPLE 5

Test for Percutaneous Absorption

The test for percutaneous absorption of the compound of formula (I) according to the present invention was conducted using the 1:1 mixed solvent of an oil (caprylic capric triglyceride) and ethanol as the carrier vehicle [see, Lehman P A, Slattery J T, Franz T J, Percutaneous absorption of retinoids: Influence of vehicle, light exposure, and dose, *J. Invest Dermatol.*, 91; 56–61, 1988]. In this test, retinol, retinol palmitate and retinoic acid which have been previously used as the raw material of pharmaceutical and cosmetic products for inhibiting skin aging were used as the comparative materials. Specifically, the dorsal skin of 8-weeks aged female mouse (naked mouse) was cut off and then 35 ml solution of the test sample was applied in an amount of 250 μl to the skin having a size of $1.7 cm^2$. Using the apparatus for measuring percutaneous absorption (Franz cell), after 24 hours, the absorbed materials were extracted respectively from 7 ml of the receptor solution [50 mM PBS buffer solution (pH=7.4) containing 2% VolPO20 Polyethylene oleyl ether (HLB=16)] and the skin and then quantitatively analyzed by high pressure liquid chromatography (HPLC). The results thus obtained are described in the following Table 1.

TABLE 1

Unit:nmol

| Part | Test sample | | | |
|---|---|---|---|---|
| | Retinol | Retinol palmitate | Retinoic acid | Compound of formula (I) (R = CH$_3$, n = 9.8) |
| Skin | 23.38 | 18.73 | 32.18 | 54.17 |
| Receptor solution | 11.48 | 0.48 | 11.40 | 62.72 |
| Total percutaneous absorption | 34.86 | 19.21 | 43.58 | 116.87 |
| Absorptivity (%) | 0.4 | 0.2 | 0.5 | 1.2 |

As can be seen from the above Table 1, the absorptivity of the compound of formula (I) according to the present invention is 3, 6 and 2.4 times as large as those of retinol, retinol palmitate and retinoic acid, which have been previously used as the agent for inhibiting skin aging, respectively. That is, it could be noted that the compound of formula (I) according to the present invention exhibits the relatively high increase in percutaneous absorption in comparison to the comparative materials.

EXAMPLE 6

Test for Collagen Synthesis

In order to determine the effectiveness of the compound of formula (I) (R=CH$_3$, n=9.8) as an agent for inhibiting skin aging, its effect for collagen synthesis was tested using retinoic acid and retinol palmitate as the comparative materials. The same count of human fibroblasts was incubated in each well of 24-well plate for 24 hours and then the test sample was applied thereto at the concentration of $10^{-4}$ to $10^{-7}$ w %/ml. After 2 hours, tritiated proline (L-2,3-$^3$H proline) was applied to the plate and then further incubated for 24 hours. The amount of collagen as newly synthesized and secreted by fibroblasts utilizing the culture medium was measured by calculating the amount of CPS (collagenous sensitive protein) on the basis of cpm (counting per minute) number of L-2,3-$^3$H proline. The result obtained by comparing the effects for collagen synthesis of the test samples on the basis of the calculated CSP amounts is shown in FIG. 1 [see, ① David F. W. and Wilson Harvey, *Analytical Biochemistry*, 1979; 96, 220–224, and ② Atsushi Hatamochi, Masashi Ono, Hiroaki Ueki and Masayoshi Namba, *J. Invest Dermatol.*, 1991, 96, 473–477]. In FIG. 1, the control group represents the group to which the serum having an activity for collagen synthesis was added instead of the material for inhibiting skin aging.

As can be seen from FIG. 1, retinol palmitate does substantially not exhibit an effect of increasing collagen synthesis and retinoic acid exhibits an increasing effect up to 21.7% at the concentration of $10^{-6}$ w %/ml. Contrary to this, the polyethoxylated compound of formula (I) according to the present invention surprisingly exhibits the highest effect (33.8%) of increasing collagen synthesis at the concentration of $10^{-7}$ w %/ml.

EXAMPLE 7

Allergy Test (LLNA)

As the safety test for the compound of formula (I) (R=CH$_3$, n=9.8), the method using ethanol as the carrier vehicle was selected [see, Kimber I (1990): Identification of contact allergens using the murine local lymph node assay, *J Appl. Toxicol.* 10(3); 173–180]. As the test samples, each of retinol palmitate and retinoic acid as the comparative materials, and the compound of formula (I) was prepared in 0.3% and 1% acetone/olive oil (4/1, v/v) solution. Each of the test sample was applied to both ears of Blab/c mouse in an amount of 50µl for 3 days and then auricular lymph node was isolated from mouse. Lymph node was micronized to monocellular state and then incubated for 24 hours with addition of radioisotope ($^3$H-thymidine). The amplification degree [cpm] of cells was measured and the results thus obtained are described in the following Table 2.

TABLE 2

| Test sample | Lymph node cell ($10^7$ cells/ml) | cpm (mean) | Amplification degree |
|---|---|---|---|
| Ethanol | 1.84 | 3078 | Carrier vehicle |
| Compound of formula (I) 0.3% | 2.82 | 3145 | 1.02 |
| Compound of formula (I) 1% | 3.02 | 7422 | 2.41 |
| Retinol palmitate 0.3% | 6.17 | 19361 | 6.29 |
| Retinol palmitate 1% | 7.27 | 21026 | 6.83 |
| Retinoic acid 0.3% | 7.82 | 22438 | 7.29 |
| Retinoic acid 1% | 8.31 | 24408 | 7.93 |

As can be seen from the above Table 2, the compound of formula (I) according to the present invention in both 0.3% and 1% solutions exhibits a low allergy induction which is three times and below as large as ethanol, whereas retinol palmitate and retinoic acid show the high allergy induction six times or more in comparison to that of ethanol under the same condition.

EXAMPLE 8

Test for Skin Irritability

In order to determine the skin irritability of the compound of formula (I) (R=CH$_3$, n=9.8) according to the present invention, the patch test using guinea pigs was conducted as follows [see, ① Draize, J. H. (1959): Dermal toxicity. Assoc. Food and Drug Officials, US. Appraisal of the safety of chemicals in Food, Drugs and Cosmetics, pp46–59, Texas State Dept. of Health, Austin, Tex. and ② Federal Register (1973): Method of testing primary irritant substances 38(187): pp1500–1541]. Six kinds of the test solutions were prepared at the concentration of 0.3% by using o/w formulation or Lexol GT-865 as the carrier vehicle. First, hair was removed from the portion (dorsal skin of mouse) for applying the test solution and then the naked portion was adapted to the environmental circumstance for 24 hours in order to minimize the skin irritability. The test solution and gauze were applied to the established portion (1.5 cm×1.5 cm) for applying the test solution, which was then sealed with the solid thin film and fixed with the elastic bandage for 48 hours in order to inhibit the evaporation and loss of the test sample. After 2 and 24 hours from removal of the closed patch (i. e. 50 and 72 hours after patch application, respectively), the degree of irritation was determined. The results thus obtained are described in the following Table 3.

TABLE 3

| Test sample | Irritation index | Degree of irritation |
|---|---|---|
| CLC | 0.7 | weak irritation |
| RPLC | 0.7 | weak irritation |

TABLE 3-continued

| Test sample | Irritation index | Degree of irritation |
| --- | --- | --- |
| RALC | 1.2 | serious irritation |
| PALC | 0.7 | weak irritation |
| RPLC #1 | 0.6 | minute irritation |
| PALC #2 | 0.6 | minute irritation |

Note)
1. CLC: Lexol GT-865
2. RPLC: Lexol GT-865 + Retinol palmitate (0.3%)
3. RALC: Lexol GT-865 + Retinoic acid (0.3%)
4. PALC: Lexol GT-865 + Compound of formula (I) (0.3%)
5. RPLC #1: O/W formulation
6. PALC #2: O/W formulation + Compound of formula (I) (0.3%)

As can be seen from the above Table 3, there is no significant difference between the irritation degrees of the compound of formula (I) according to the present invention, retinol palmitate and retinoic acid.

EXAMPLE 9
Test for Organ Incubation of Skin

In order to determine the primary safety of the compound of formula (I) (R=CH$_3$, n=9.8) according to the present invention, the test was conducted using 9-weeks aged naked female mouse as follows. Seven kinds of the test solution were prepared using Lexol GT-865 as the carrier vehicle and then MTT [3-(4,5-dimethylthiazole-2,5-diphenyltetrazolium bromide] assay was conducted [see, J. J. M. Van De SandT, A. A. J. J. L. Rutten & H. B. W. M. Koeter., Cutaneous toxicity testing in organ culture: Neutral Red uptake & Reduction of tetrazolium salt (MTT) Toxic. In Vitro Vol. 7, No. 1, 81–86, 1993]. The results thus obtained are described in the following Table 4.

TABLE 4

| Test sample | | Degree of irritation | Safety |
| --- | --- | --- | --- |
| — | | 0.46 | no irritation |
| Control group | <0.05% Sodium lauryl sulfate | 0.35 | minute irritation |
| | <0.25% Sodium lauryl sulfate | 0.24 | moderate irritation |
| | <0.5% Sodium lauryl sulfate | 0.10 | strong irritation |
| Lexol GT-865/0.3% Retinol palmitate | | 0.34 | minute irritation |
| Lexol GT-865/0.3% Retinoic acid | | 0.11 | strong irritation |
| Lexol GT-865/0.3% Compound of formula (I) | | 0.27 | weak irritation |
| 100% Lexol GT-865 | | 0.34 | minute irritation |

As can be seen from the above Table 4, 0.3% retinoic acid exhibits a strong irritation, whereas retinol palmitate and the compound of formula (I) exhibit the similar weak irritation at the same concentration.

EXAMPLE 10
Cytotoxicity Test

Figure 2:
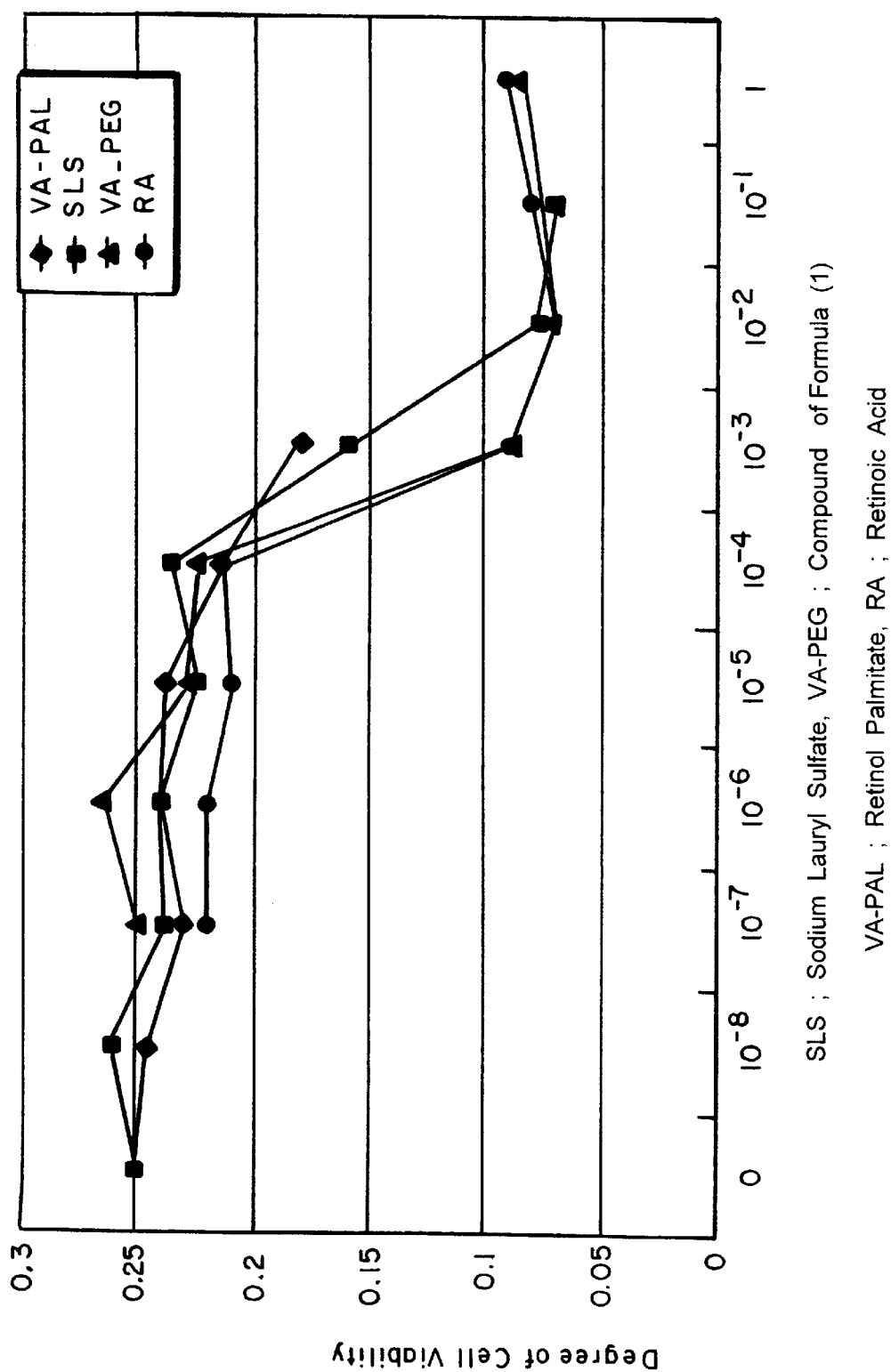
FIG. 2 shows the cytotoxic effect of the compound of formula (I) according to the present invention in comparison to those of retinoic acid and retinol palmitate as the comparative materials.

In order to confirm the primary safety of the compound of formula (I) (R=CH$_3$, n=9.8) for use as the raw material in pharmaceutical and cosmetic products, the cytotoxicity of the compound of formula (I) was tested by incubating the compound (I) with V79-4 cells (continuous cell line of lung fibroblast of Chinese hamster) and then conducting MTT assay [see, Mossman T. (1983), Rapid colorimetric assay for cellular growth & survival: application to proliferation & cytotoxicity assays, Journal of Immunological Methods 65, 55–63]. The results thus obtained are shown in FIG. 2.

As can be seen from the results depicted in FIG. 2, the compound of formula (I) according to the present invention exhibits gradually at the concentration of $10^{-3}$ w %/ml or more but shows only a weak toxicity at the concentration of $10^{-4}$ w %/ml and below. This result is well consistent with the results depicted in FIG. 1 showing that the compound of formula (I) begins to display the effect of increasing collagen synthesis at the concentration below $10^{-4}$ w %/ml as the limiting concentration at which any toxicity is not caused, and exhibits the highest effect of increasing collagen synthesis at the concentration of $10^{-7}$ w %/ml but does not exhibit any increasing effect at the cytotoxic concentration of $10^{-3}$ w %/ml or more.

What is claimed is:

1. A polyethoxylated retinamide derivative represented by the following formula (I):

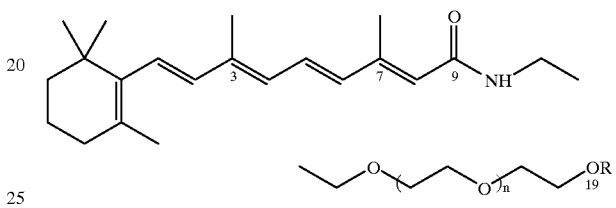

in which

R represents hydrogen or C$_{1-6}$-lower alkyl and n denotes the number of 2 to 100.

2. The compound according to claim 1, wherein R is hydrogen or methyl and n denotes the number of 4 to 40.

3. A process for preparing the compound of formula (I) as defined in claim 1 which comprises:

1) reacting a compound of formula (IIa):

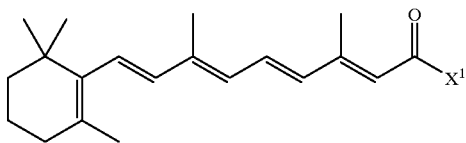

wherein X$^1$ represents halogen, with a mono-methoxy polyethylene glycol amine of formula (IIIa):

wherein R and n are defined as in claim 1, in a solvent in the presence of an organic amine catalyst, or 2) reacting a compound of formula (IIb):

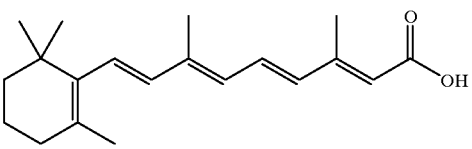

with a compound of formula (IIIa):

(IIIa)

wherein R and n are defined as in claim 1, in a solvent in the presence of a condensing agent and a catalyst, or 3) reacting a compound of formula (IIc):

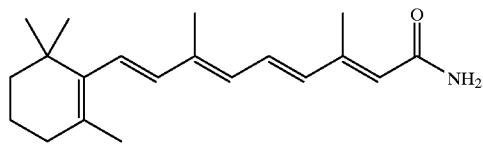
(IIc)

with a mono-methoxy polyethylene glycol halide or sulfonate of formula (IIIb):

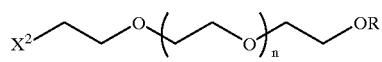
(IIIb)

wherein R and n are defined as in claim 1 and $X^2$ is halogen, p-toluenesulfonyl or methanesulfonyl, in a solvent in the presence of a base.

4. The process according to claim 3, wherein in the variant 1) the organic amine catalyst is pyridine or triethylamine and is used in the ratio of 1.0 to 2.0 moles with respect to one mole of the compound of formula (IIIa).

5. The process according to claim 3, wherein in the valiant 2) the condensing agent is N,N-dicyclohexylcarbodiimide (DCC) or N,N-carbonyldiimidazole (CDI).

6. The process according to claim 3, wherein in the variant 2) the catalyst is N,N-dimethylaminopyridine(DMAP) or 1-hydroxybenzo-triazole(HOBT).

7. The process according to claim 3, wherein in the variant 3) the base is one or more selected from the group consisting of sodium hydride, sodium hydroxide, sodium carbonate, potassium hydride, potassium carbonate, pyridine and triethylamine.

8. The process according to claim 3, wherein the solvent is one or more selected from the group consisting of dichloromethane, benzene, toluene, tetrahydrofuran and diethyl ether.

9. A cosmetic composition which comprises an effective component the compound of formula (I) as defined in claim 1.

* * * * *